(12) United States Patent
Peruzzo (10) Patent No.: US 11,931,542 B2
(45) Date of Patent: Mar. 19, 2024

(54) NEST FOR SUPPORTING A PLURALITY OF MEDICAL CONTAINERS, A MEDICAL CONTAINER PACK COMPRISING THIS NEST, AND A METHOD FOR MANUFACTURING A MEDICAL CONTAINER

(71) Applicant: Becton Dickinson France, Le Pont de Claix (FR)

(72) Inventor: Grégory Peruzzo, Prunieres (FR)

(73) Assignee: Becton Dickinson France, Le Pont de Claix (FR)

( * ) Notice: Subject to any disclaimer, the term of this patent is extended or adjusted under 35 U.S.C. 154(b) by 730 days.

(21) Appl. No.: 17/051,902

(22) PCT Filed: Apr. 24, 2019

(86) PCT No.: PCT/EP2019/060510
§ 371 (c)(1),
(2) Date: Oct. 30, 2020

(87) PCT Pub. No.: WO2019/211139
PCT Pub. Date: Nov. 7, 2019

(65) Prior Publication Data
US 2021/0106749 A1    Apr. 15, 2021

(30) Foreign Application Priority Data
May 2, 2018    (EP) .................................. 18305547

(51) Int. Cl.
*A61M 5/00*    (2006.01)
*A61M 5/31*    (2006.01)
(Continued)

(52) U.S. Cl.
CPC .......... *A61M 5/008* (2013.01); *A61M 5/3135* (2013.01); *A61M 5/3137* (2013.01);
(Continued)

(58) Field of Classification Search
CPC ........ A61M 5/00; A61M 5/002; A61M 5/008; A61M 5/31; A61M 5/3135; A61M 5/3137;
(Continued)

(56) References Cited

U.S. PATENT DOCUMENTS 2,510,091 A    6/1950    Dofsen et al.
3,114,455 A *  12/1963   Stagg .................. A61M 5/3202
                                                  206/366
(Continued)

FOREIGN PATENT DOCUMENTS

| FR | 2614658 A1 | 11/1988 |
| JP | 2012100927 A | 5/2012 |
| JP | 2013538627 A | 10/2013 |
| WO | 9206725 A1 | 4/1992 |
| WO | 2012035909 A1 | 3/2012 |

*Primary Examiner* — Bryon P Gehman
(74) *Attorney, Agent, or Firm* — The Webb Law Firm (57) ABSTRACT

This nest comprises a plurality of breakable connecting bridges, a plurality of flanges arranged in a predetermined pattern and configured to form the flanges of the medical containers, the flanges being connected to the breakable connecting bridges, and a supporting structure attached to the breakable connecting bridges so as to support the flanges. The flanges are integrally formed with the breakable connecting bridges and the supporting structure.

15 Claims, 6 Drawing Sheets

(51) Int. Cl.
*B65B 3/00* (2006.01)
*B65D 21/02* (2006.01)

(52) U.S. Cl.
CPC .......... *B65B 3/006* (2013.01); *B65D 21/0201* (2013.01); *A61M 2005/3139* (2013.01); *A61M 2005/3142* (2013.01); *B65B 2230/02* (2013.01)

(58) Field of Classification Search
CPC .. A61M 2005/3129; A61M 2005/3139; A61M 2005/3142; B65B 3/00; B65B 3/006; B65B 2230/02; B65D 21/02; B65D 21/0201; B65D 25/10; B65D 25/108; B65D 71/50
USPC ........................................................ 206/366
See application file for complete search history.

(56) References Cited

U.S. PATENT DOCUMENTS

| | | | |
|---|---|---|---|
| 5,372,590 A | 12/1994 | Haber et al. | |
| 8,196,741 B2* | 6/2012 | Finke | A61M 5/008 |
| | | | 206/366 |
| 8,522,975 B2* | 9/2013 | Finke | A61M 5/008 |
| | | | 206/366 |
| 8,939,288 B2 | 1/2015 | Gagnieux et al. | |
| 9,211,375 B2* | 12/2015 | Finke | A61M 5/008 |
| 10,888,937 B2* | 1/2021 | Dieter | B23D 33/025 |
| 2012/0118777 A1* | 5/2012 | Kakiuchi | A61M 5/002 |
| | | | 206/366 |
| 2012/0180286 A1 | 7/2012 | Dieter et al. | |
| 2013/0313143 A1 | 11/2013 | Finke et al. | |

\* cited by examiner

NEST FOR SUPPORTING A PLURALITY OF MEDICAL CONTAINERS, A MEDICAL CONTAINER PACK COMPRISING THIS NEST, AND A METHOD FOR MANUFACTURING A MEDICAL CONTAINER

CROSS-REFERENCE TO RELATED APPLICATIONS

This application is the United States national phase of International Application No. PCT/EP2019/060510 filed Apr. 24, 2019, and claims priority to European Patent Application No. 18305547.4 filed May 2, 2018, the disclosures of which are hereby incorporated by reference in their entirety.

BACKGROUND OF THE INVENTION

The present invention relates to a holding device for supporting a plurality of medical containers, a medical container pack including this holding device, and to a method for manufacturing a medical container.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a container supported by the holding device of the invention, and the "proximal direction" is to be understood as meaning the opposite direction to said direction of injection, that is to say the direction towards the user's hand holding a container as for an injection operation.

Medical containers, such as pre-fillable or prefilled syringes, often need to be transported from one site to another site, for instance from a manufacturing site to a second site where the medical containers may be filled with a pharmaceutical composition agent, such as a vaccine, a medicine or a therapeutic agent. Less frequently, the medical containers may be manufactured and filled in the same first site and then be transported to a storage site. During transportation, the medical containers are usually held by a holding device, also called a nest. The nest is placed inside a box-shaped tub which has one opening sealed by a sealing cover. Removal of the medical containers from this tub basically requires peeling off the sealing cover, removing the nest holding the medical containers from the tub and then removing the medical containers from the nest by axially sliding the medical containers relative to the nest. Before being removed from the nest and packaged individually, the medical containers are filled with a pharmaceutical composition agent by means of a filling machine.

The nest is a plate-shaped tray that is generally configured to support more than one hundred medical containers. Usually, the nest comprises several holes aligned according to predetermined rows, each hole being configured to permit insertion of the barrel of one medical container, until the flange of the medical container rests on one face of the plate-shaped nest.

However, the medical containers can slightly move relative to the nest during transportation or when the nests are processed on the filling lines. As a result, the medical containers may not be properly centered relative to the filling needle when filled with a pharmaceutical composition agent. Besides, syringe denesting may occur on filling lines. During transportation, the clearance may entail shocks between adjacent containers, sometimes leading to cosmetic defects and even container breakages.

Furthermore, a medical container such as a syringe typically comprises an elongated barrel defining a reservoir for containing the pharmaceutical composition agent, a plunger stopper located inside the barrel, a plunger to move the plunger stopper inside the barrel and expel the pharmaceutical composition agent through a tip closed by a staked needle and/or needle shield at a distal end of the barrel, and a flange at a proximal end of the barrel. The flange provides a surface for positioning a user's fingers, generally the index and the middle fingers, while the plunger rodis activated with the thumb. Medical containers may be made of glass or plastic material.

The flange is formed before the tip during the manufacturing process of a glass medical container. Then, the flange acts as a support and reference when forming the tip. However, the flange is not always perfectly planar. Therefore, there might be some inaccuracy when forming the tip. This may result in an increased dead volume or an imperfectly controlled syringe length. By dead volume, it should be understood the volume of the pharmaceutical composition agent remaining in the tip after transfer of the pharmaceutical composition agent from the syringe to another device. It is desirable for the dead volume to be as small as possible in order, on the one hand, to minimize the wastage of pharmaceutical composition agent and, on the other hand, for reasons of accuracy of the volume of pharmaceutical composition agent administered.

SUMMARY OF THE INVENTION

An aspect of the invention is a holding device for supporting medical containers, said holding device allowing an improved centering of the medical containers on the filling lines, thereby preventing medical containers from denesting or breakage on filling lines or during transportation, and also enabling to reduce the dead volume and better control the length of the medical containers.

An aspect of the invention is a holding device for holding a plurality of medical containers, said holding device comprising:
- a plurality of breakable connecting bridges,
- a plurality of flanges arranged in a predetermined pattern and configured to form the flanges of said medical containers, said flanges being connected to said breakable connecting bridges,
- a supporting structure attached to said breakable connecting bridges in order to support said plurality of flanges,
- wherein the flanges are integrally formed with the breakable connecting bridges and the supporting structure.

This holding device enables an improved centering of the medical containers on the filling lines, because the flange of the medical containers is attached to the supporting structure by means of the breakable connecting bridges. Since the flanges are fixedly attached to the supporting structure, this also prevents the medical containers from receiving shocks during filling operation or during transportation.

The holding device may refer to a nest.

Advantageously, the breakable connecting bridges comprise a first end portion attached to one of the flanges and a second end portion attached to another flange or to the supporting structure.

Advantageously, the first end portion has a decreasing thickness towards the flange.

Advantageously, the second end portion has a decreasing thickness towards the other flange or the supporting structure.

These features result in a smooth flange edge after breaking of the connecting bridge.

Advantageously, the breakable connecting bridges comprises an intermediate portion interposed between the first and the second end portions.

The flanges are preferably attached to the supporting structure by the breakable connecting bridges.

Advantageously, at least some adjacent flanges are separated from each other by one or several breakable connecting bridges only.

Therefore, these flanges are directly connected to an adjacent flange by at least one of the breakable connecting bridges.

This enables to increase the number of flanges held by the holding device per unit of area.

In an embodiment, the supporting structure is a plate-shaped nest. The flanges may be plate-shaped. The flanges and the nest may be coplanar.

Advantageously, the supporting structure delimits a plurality of through-openings, each flange extending inside one of said through-openings.

In an embodiment, each flange is surrounded by a segmented groove.

Advantageously, each flange is surrounded by at least two slots, two successive slots being separated by a breakable connecting bridge. The slots extend between the supporting structure and the flanges. The slots surrounding a flange thus form the segmented groove.

In an embodiment, each flange is connected to the supporting structure by at least two breakable connecting bridges, and preferably by three, more preferably by four breakable connecting bridges. This enables to hold the flanges in a stable and planar configuration.

In an embodiment, the supporting structure comprises a peripheral edge, said peripheral edge being connected to peripheral flanges of the plurality of flanges by breakable connecting bridges.

The peripheral edge allows handling of the holding device on filling lines or during transportation, while stiffening the holding device so as to hold the flanges in a same plane.

In an embodiment, the supporting structure comprises reinforcing bars extending between adjacent rows of flanges.

This enables to stiffen the supporting structure and thus maintain the supporting structure in a planar distribution for improved accuracy on the filling lines.

In an embodiment, the reinforcing bars extend beneath the breakable connecting bridges interposed between said two rows of flanges. This allows holding the flanges closer so that the holding device holds more flanges per unit of area. More precisely, the reinforcing bars may be attached to the intermediate portion of the breakable connecting bridges.

Advantageously, the reinforcing bars are attached to the nest. The reinforcing bars extend at one side of said nest.

Advantageously, the reinforcing bars are higher than wide.

The reinforcing bars may have a rectangular cross section shape.

Advantageously, the supporting structure comprises a first set of reinforcing bars parallel to a first direction and a second set of reinforcing bars parallel to a second direction which intersects said first direction.

In an embodiment, the holding device comprises securing means configured to secure a barrel of one of said medical containers to said flange. This enables to secure the medical containers to the holding device, so that the medical containers cannot move on filling lines or during transportation, while forming the medical containers.

In an embodiment, the securing means comprise a guiding conduit extending from each flange, said guiding conduit being configured to receive the barrel. This provides a better centering on the filling lines.

The guiding conduit may be provided with a securing element configured to secure a barrel, for example a barrel made of a glass material, to the flange.

In embodiments:
the guiding conduit comprises an attachment surface configured to receive an adhesive so as to secure the barrel to the flange,
the guiding conduit comprises a friction-fit surface configured to secure the barrel to the flange. Advantageously, the friction-fit surface is made of a thermoplastic elastomer or in rubber. Advantageously, the guiding conduit comprises a ring attached to the flange, the friction-fit surface being provided on an inner wall of this ring. Advantageously, this ring is inserted in a groove of the guiding conduit,
the guiding conduit comprises a clipping element configured to fit a complementarily shaped-clipping element provided on the barrel.

Advantageously, each flange comprises an axial stop configured to block insertion of the barrel into the guiding conduit. This provides accurate positioning of the barrel.

Advantageously, the axial stop comprises a tapered lateral surface. This allows a better centering on filling lines.

Another aspect of the invention is a medical container pack comprising the holding device and the plurality of medical containers, wherein the medical containers have a barrel made of glass and wherein said barrel is secured to one of the flanges of the holding device.

As a result, each medical container is properly secured to the holding device, thus providing an improved centering on filling lines, and is detachable from this supporting structure by breaking the corresponding connecting bridges.

Another aspect of the invention is a medical container pack comprising the holding device and the plurality of medical containers, wherein the medical containers have a barrel made of a plastic material and wherein said barrels and the holding device are molded in a single piece. As a result, the barrels are integrally formed with the holding device. The barrels and the holding device are a single piece.

Another aspect of the invention is a method for manufacturing a medical container, comprising the steps of:
providing a medical container pack as above described,
breaking the connecting bridges securing one of the flanges to the supporting structure so as to detach the corresponding medical container from the medical container pack.

Advantageously, the method comprises the step of inserting barrels into an opening of the flanges and securing said barrels to the flanges in order to form the medical container pack.

Advantageously, the method comprises the step of molding barrels and the flanges in a single piece so as to form the medical container pack. Advantageously, the method comprises a previous step of positioning needles in the mold so that each barrel is overmolded onto one of said needles during the step of molding the barrels and the flanges in a single piece.

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

Figure 1:
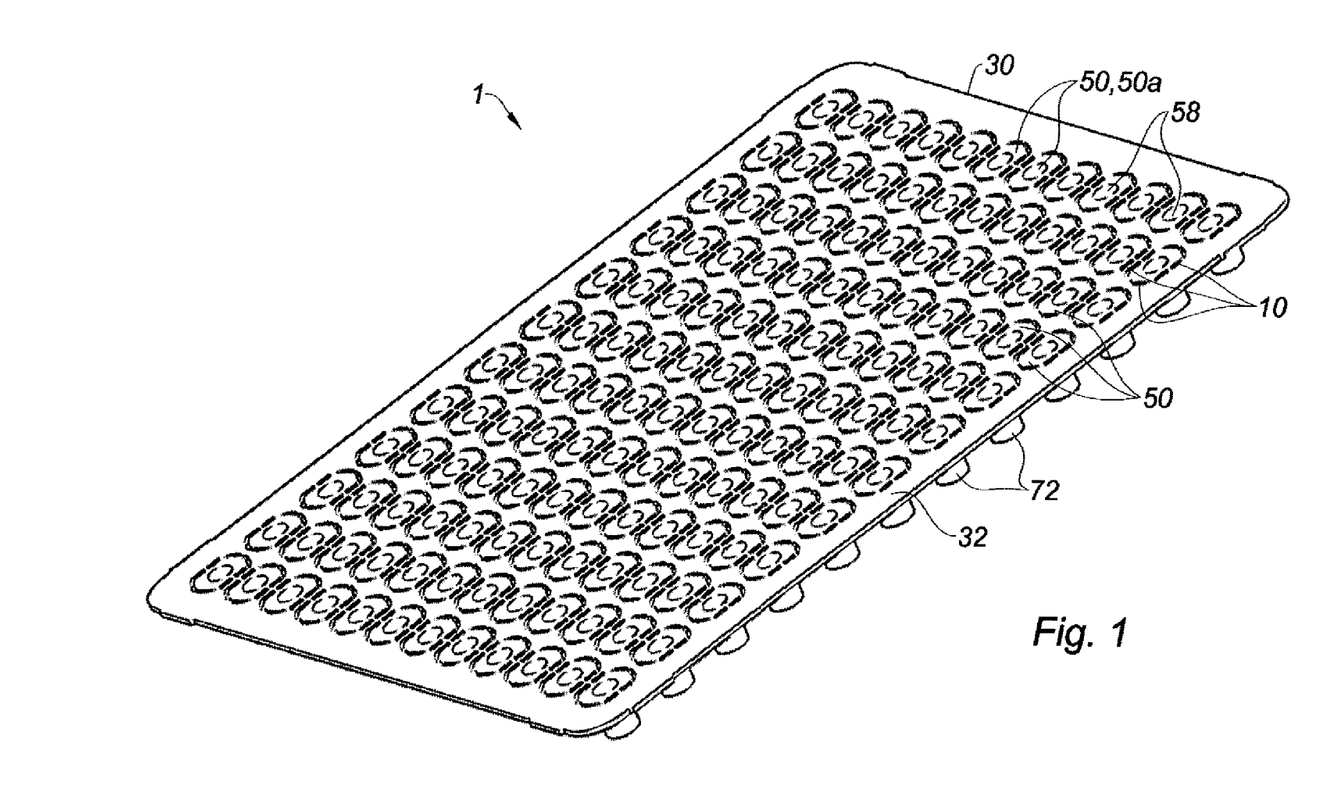
FIG. 1 is a perspective view of a holding device according to an embodiment of the invention.

With reference to FIG. 1, is shown a holding device 1 according to the invention. The holding device 1 is configured to concurrently support a plurality of medical containers 100, as shown on FIG. 4. The holding device 1 therefore serves as a nest for packaging, storing, transporting and handling on a filling line of the medical containers 100. It should be noted that the medical containers 100 may be syringes, such as pre-fillable syringes. The medical containers 100 are intended, after filling, to contain a pharmaceutical composition such as a vaccine, a medicine or a therapeutic pharmaceutical composition.

The holding device 1 comprises a plurality of breakable connecting bridges 10, a supporting structure 30, said breakable bridges 10 being attached to the supporting structure 30, and a plurality of flanges 50 which are configured to form the flanges 50 of said medical containers 100, as will be described in further details below.

The breakable connecting bridges 10 connect each flange 50 to another adjacent flange 50 or to the supporting structure 30, so that the flanges 50 are held together according to a predetermined pattern. As shown on FIG. 2, the flanges 50 may be aligned in parallel rows. Besides, the flanges 50 preferably extend in the same plane, so that the holding device substantially has a plate-shaped configuration.

The breakable connecting bridges 10 are configured to be cut or broken when a sufficient force is exerted upon them, in order to permit the flanges 50 to be separated from the supporting structure 30. As a result, the flanges 50 are connected to the connecting bridges 10, and thus to each other and/or to the supporting structure 30, in a detachable manner.

The flanges 50 are separated from the supporting structure 30 by means of the breakable connecting bridges 10. Each flange 50 is thus attached to the holding device 1 by breakable connecting bridges 10 only.

Figure 2:
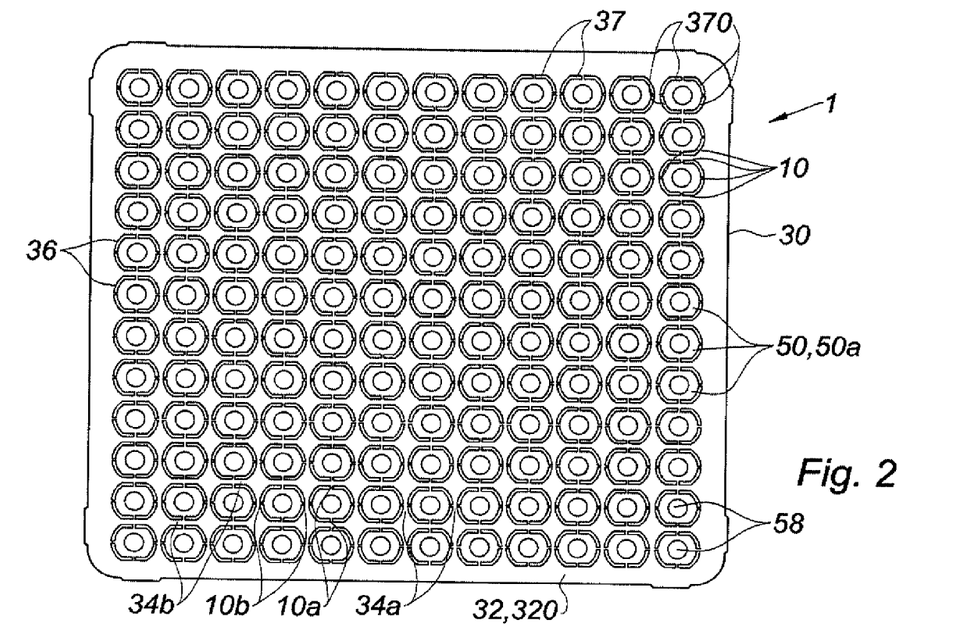
FIG. 2 is a top view of a holding device according to an embodiment of the invention.

As shown on FIG. 2, each flange 50 is surrounded by a segmented groove 37. The groove 37 is a through opening. The segmented groove 37 is crossed by the breakable connecting bridges 10 configured to link the flange 50 to the supporting frame 30. The groove 37 extends between the corresponding flange 50 and the supporting structure 30.

Each flange 50 may be surrounded by at least two slots 370, two successive slots 370 being separated by a breakable connecting bridge 10. The slots 370 extend between the supporting structure 30 and the flanges 50. The slots 370 surrounding a flange 50 thus form the segmented groove 37.

The supporting structure 30 is configured to maintain the flanges 50 in a fixed position as long as the flanges 50 are connected to this supporting structure 30 by the breakable connecting bridges 10. Therefore, the supporting structure 30 forms stiffening means for fixedly supporting the plurality of flanges 50.

The supporting structure 30 connects all or at least several of the breakable connecting bridges 10. For example by extending between adjacent connecting bridges 10, as shown on FIG. 1, or by extending on or beneath the connecting bridges 10, as shown on FIG. 5B. As a result, each flange 50 may be connected to the supporting structure 30, or each flange 50 may be connected to an adjacent flange 50 by at least one of the breakable connecting bridges 10.

According to one preferred embodiment, the supporting frame 30 is a plate comprising a plurality of through-openings 36. At least one flange 50 extends in each trough-opening 36, the flange 50 being connected to the supporting frame 30 by at least two breakable connecting bridges 10, and preferably by three, more preferably by four breakable connecting bridges 10. The plate is preferably rectangular.

The flanges 50 are integrally formed with the breakable connecting bridges 10 and the supporting structure 30. In other words, the flanges 50, the breakable connecting bridges 10 and the supporting structure 30 is a single piece. As a result, the holding device 1 is a nest with integrated syringe flanges 50.

Preferably, the flanges 50, the breakable connecting bridges 10 and the supporting frame are in a plastic material, such as polypropylene. The flanges 50, the breakable connecting bridges 10 and the supporting structure 30 are molded in a single piece.

The flanges 50 are configured to serve as the flange 50 of the medical containers 100. The flanges 50 may be plate-shaped. They may have two opposite planar faces 52, 54, namely a proximal face 52 and a distal face 54. The proximal face 52 may serve as a push surface for applying a force on the flange 50 in order to break the connecting bridges 10 attached to this flange 50. This force may alternatively be applied onto the distal face 54. The distal face 54 is configured to receive a user's fingers (generally the index and middle fingers) when the medical container 100 is being used. The proximal and distal faces 52, 54 are joined by a peripheral side edge 56. As can be seen on FIG. 5B, the breakable connecting bridges 10 are preferably fixed to the edge 56 of the flanges 50. The flanges 50 delimit a central opening 58. The central opening 58 is configured to receive a plunger rod of the medical container 100. The flanges 50 preferably comprises two diametrically opposite arms 60 which radially extend in order to provide a sufficient reception area for the user's fingers. These two arms 60 may be joined by two diametrically opposite lateral portions 62. The lateral portions 62 are thinner than the arms 60 so as to improve compactness of the flanges 50 so that the holding device 1 comprise more flanges 50 per unit area.

Figure 5A:
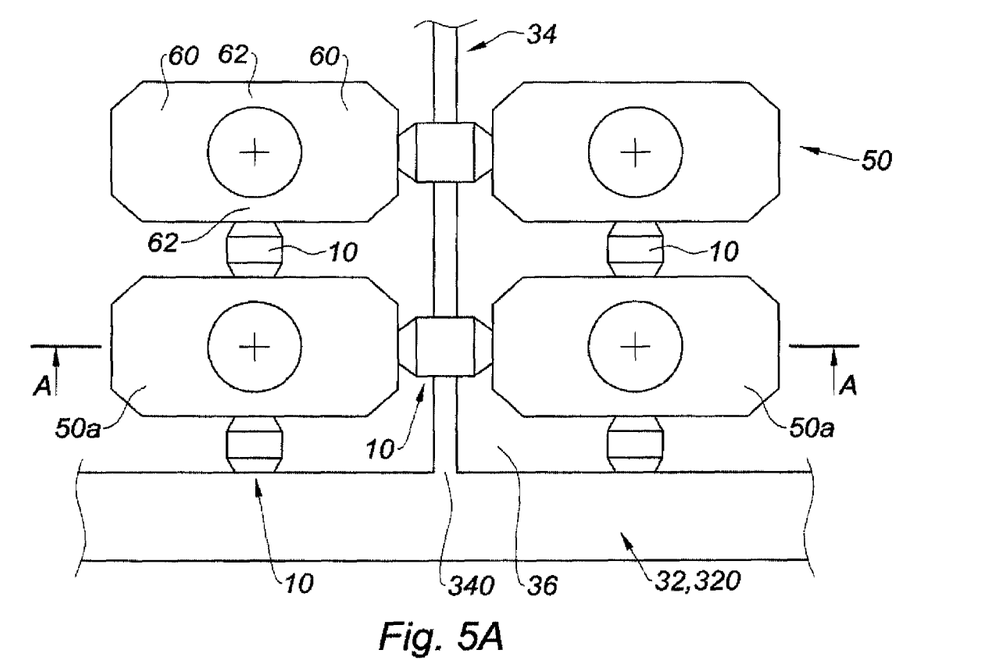
FIG. 5A is a top view of a part of a holding device according to an embodiment of the invention.
Figure 5B:
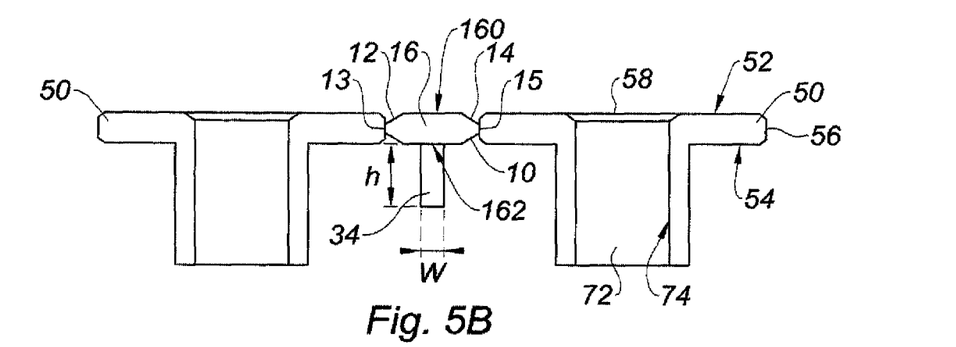
FIG. 5B is a cross-section view along line A-A of FIG. 5A, and FIGS. 6A, 6B, 6C, 6D are cross-section views of part of a holding device according to different embodiments of the invention.

The breakable connecting bridges 10 are configured to break so as to allow separation of the flanges 50. The breakable connecting bridges 10 may be rods having one end fixed to one of the flanges 50 and an opposite end fixed to an adjacent flange 50 or to the supporting structure 30. With reference to FIG. 5B, the breakable connecting bridges 10 may more precisely comprise a first end portion 12 attached to one of the flanges 50 and a second end portion 14 which is opposite the first end portion 12, this second end portion 14 being fixed to another flange 50 or to the supporting structure 30. The breakable connecting bridges 10 may also comprise an intermediate portion 16 which connects the first and second end portions 12, 14. The first end portion 12 may have a decreasing cross section until this first end portion 12 reaches the flange 50. Similarly, the second end portion 14 may have a decreasing cross section until this second end portion 14 reaches the other flange 50 or the supporting structure 30. The first end portion 12 and the second end portion 14 each have an apex 13, 15. These apex 13, 15 are the thinnest parts of the bridges 10 and may be the sole parts of the connecting bridges 10 which contact the flanges 50 or the supporting structure 30. The apex 13, 15 may be a point or a line contact, more precisely a straight line contact. As shown on the FIGS. 5A and 5B, this line contact preferably extends parallel to the rows of flanges 50. The first and/or second end portions 12, 14 may have a conical or pyramidal shape. The intermediate portion 16 may have a cross section greater or equal to the largest cross section of the first or second end portions 12, 14. This intermediate portion 16 may have a cylindrical or parallel-epipedal shape. As shown on FIGS. 5A and 5B, the intermediate portion 16 has a proximal face 160 and a distal face 162.

It should be noted that the breakable connecting bridges 10 may longitudinally extend perpendicular or parallel to the rows of flanges 50, as shown on FIG. 2 where the breakable connecting bridges 10 are arranged either vertically or horizontally.

With reference to FIG. 2, each flange 50 may be connected to adjacent flanges 50 or to the supporting structure 30 by two pairs of breakable connecting bridges 10. These two pairs include a first pair of connecting bridges 10a which are parallel to a first direction, and a second pair of connecting bridges 10b which are parallel to a second direction orthogonal to the first direction. More precisely, the first and second directions are parallel to orthogonal rows of flanges 50.

The supporting structure 30 is configured to hold the flanges 50 together and fixed relative to each other. As mentioned above, the supporting structure 30 may be plate shaped. More precisely, the supporting structure 30 has a rectangular plate shape. As shown on the Figures, the supporting structure 30 may comprise a peripheral edge 32 surrounding the flanges 50. This peripheral edge 32 has one or several longitudinal beams or plate-shaped bands 320, each lining one side of the plurality of flanges 50, which may be connected to each other at corners. The peripheral edge 32 is connected to a set of peripheral flanges 50a by means of breakable connecting bridges 10. The peripheral flanges 50a are the outermost flanges 50 of the plurality of flanges 50.

The supporting structure 30 may comprise reinforcing bars 34 extending between adjacent rows of flanges 50. The reinforcing bars 34 have preferably two opposite ends 340 which are fixed to the peripheral edge 32. The reinforcing bars 34 preferably extend in a straight direction. As visible on FIG. 5B, the reinforcing bars 34 advantageously have a rectangular cross section. Their height h may be greater than their width w.

As above-mentioned, the supporting structure 30 may delimit a plurality of openings 36, each opening 36 receiving at least one of the flanges 50. As shown on FIG. 5A, the openings 36 may be delimited by adjacent reinforcing bars 34. With reference to FIGS. 1 to 4, each opening 36 receives only one flange 50. With reference to FIG. 5A, each opening 36 receives a full row of flanges 50 or a part of a row of flanges 50.

In an embodiment not shown, the reinforcing bars 34 may extend on one side of the plate-shaped nest forming the supporting structure 30 of FIGS. 1 to 4.

As shown on FIG. 5B, the reinforcing bars 34 may alternatively be fixed to an intermediate portion 16 of the connecting bridges 10 which directly connect two adjacent rows of flanges 50. For example, the reinforcing bars 34 extend on or preferably beneath these breakable connecting bridges 10, that is to say against a proximal face 160 or a distal face 162 of the breakable connecting bridges 10.

Figure 3:
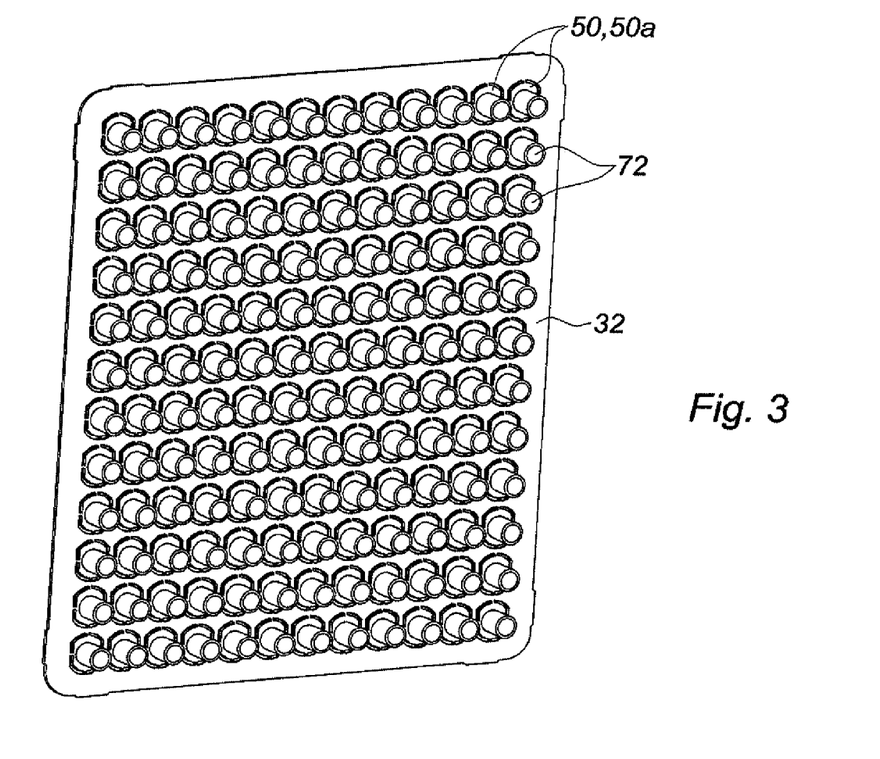
FIG. 3 is a perspective view of a holding device according to an embodiment of the invention.

The flanges 50 advantageously comprises securing means configured to fix a barrel 102 of one of said medical containers 100 to each flange 50. With reference to FIG. 3, the securing means preferably comprise a guiding conduit 72. The guiding conduit 72 extends from the opening 58. The guiding conduits 72 are configured to receive and guide insertion of the barrels 102 inside the openings 58, this insertion occurring in a direction orthogonal to the flanges 50. The guiding conduits 72 are tubular and for example have a cylindrical shape. Preferably, the guiding conduits 72 extend from the distal face 54 of the flanges 50. The guiding conduits 72 define an internal wall 74. The internal wall 74 may comprise an annular recess or groove 740 which is configured to receive a securing element 76 in order to fix the barrels 102 to the flanges 50. The sleeves may be molded with the flanges 50 in a single piece.

Figure 6A:
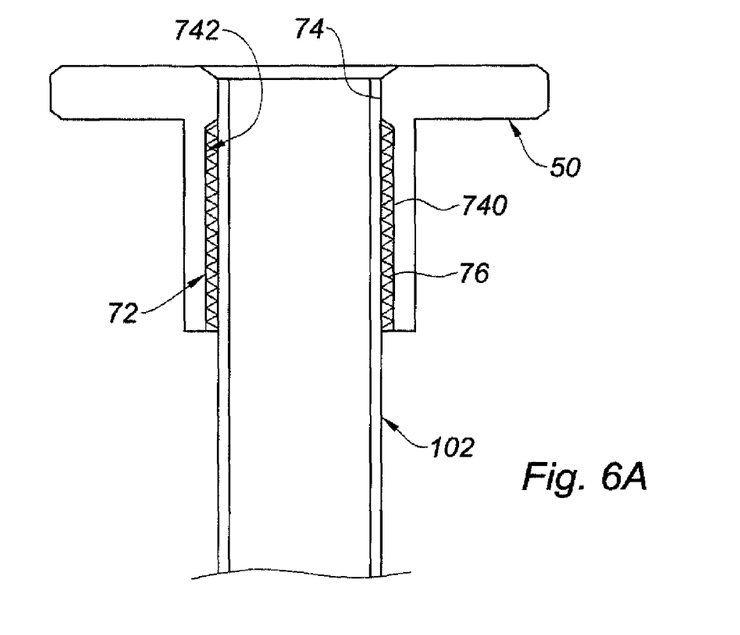

With reference to FIG. 6A, the securing element 76 may be an adhesive applied on a surface 742 of the groove 740. The surface 742 thus forms an attachment surface configured to receive an adhesive. As a result, the barrel 102 may be glued into the guiding conduit 72.

Figure 6B:
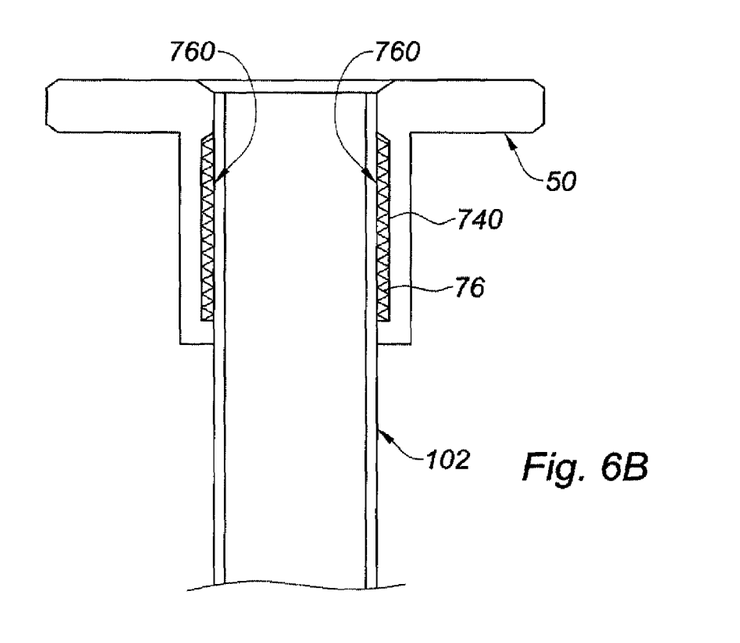

With reference to FIG. 6B, the securing element 76 may be an internal friction-fit surface 760 which is configured to adhere to the barrel 102. This friction-fit surface 760 and the barrel 102 have an adhesive coefficient greater than an adhesive coefficient between the rest of the guiding conduit 72 and the barrel 102. This-friction-fit surface 760 a may be arranged on an insert, for example a ring, which is accommodated inside the recess or groove 740 and which may be made of a thermoplastic elastomer or rubber. Alternatively, the friction-fit surface 760 may be made of a thermoplastic elastomer realized by co-injection molding.

Figure 6C:
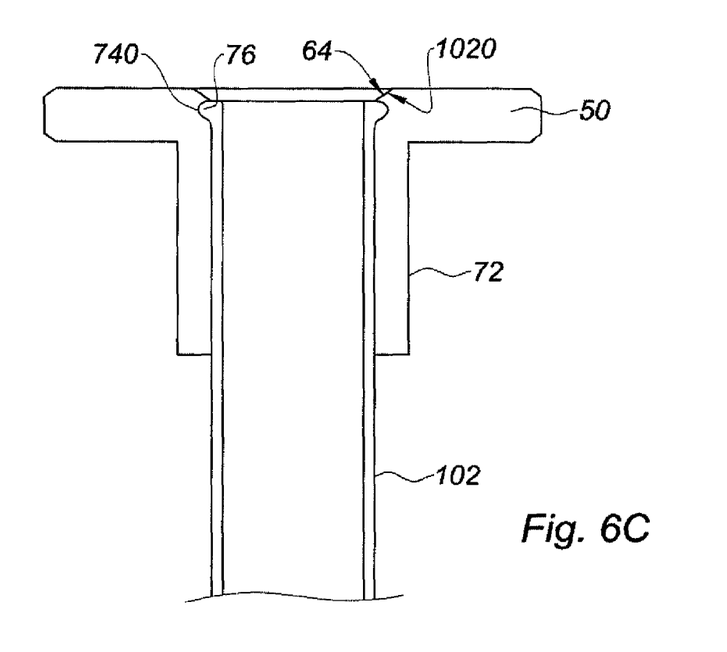

With reference to FIG. 6C, the securing element 76 may be a snap feature. The snap feature may be an annular rib provided on a lateral wall of the barrel 102. This rib has a shape complementary to the shape of the groove 740 and is configured to be inserted into said groove 740 in order to fix the barrel 102 to the flange 50. The rib and the groove 740 thus form clipping elements configured to fix the barrel 102 to the flange 50.

The securing means may be provided with an axial stop configured to block insertion of the barrel 102 through the flange 50, for example once the barrel 102 is fully inserted. The axial stop may be a tapered lateral surface 64 provided in an inner edge delimiting the opening 58. The barrel 102 may include a proximal end provided with a tapered lateral surface 1020 configured to lean against the surface 64 when the barrel 102 is introduced inside the opening 58.

Figure 4:
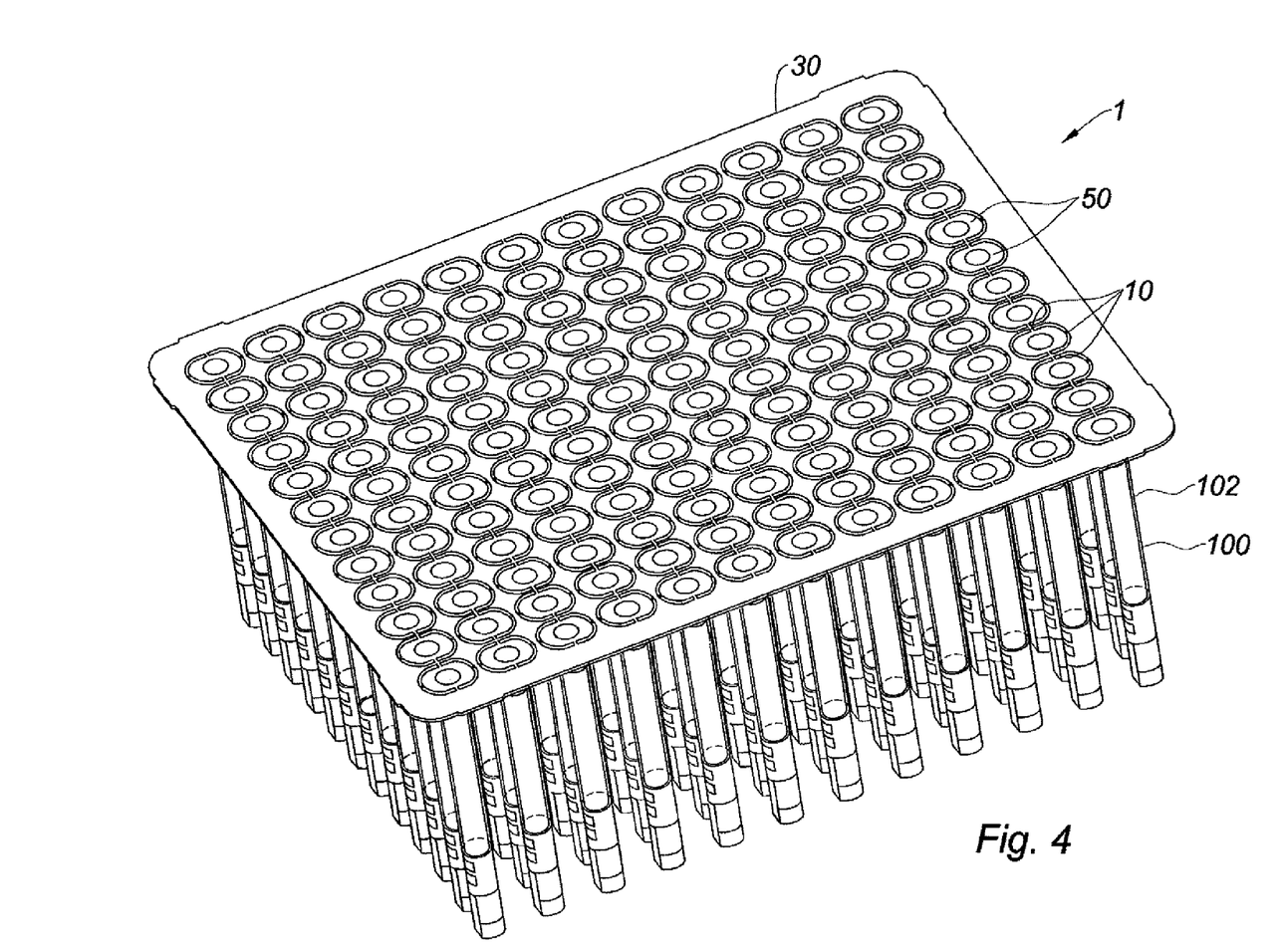
FIG. 4 is a perspective view of a holding device according to an embodiment of the invention.
Figure 6D:
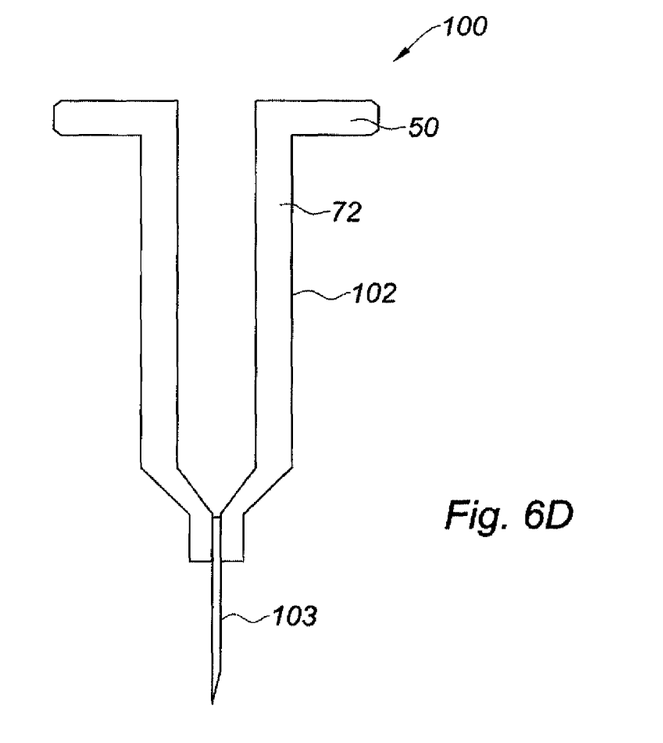

With reference to FIG. 4, is shown a pack of medical containers including the holding device 1 and the plurality of medical containers 100. These medical containers 100 are secured to the flanges 50 which are fixed to the nest in a detachable manner. The medical containers 100 have a barrel 102 defining a reservoir for the pharmaceutical composition, said barrel 102 having a proximal end attached to one of the flanges 50 and a distal end provided with a distal tip, said distal tip defining a fluid passageway in communication with said reservoir. In an embodiment, the barrel 102 is made of glass and is secured to the corresponding flange 50 by the securing means. In another embodiment, the barrel 102 is made of a plastic material and is molded with the flanges 50, the supporting structure 30 and the breakable connecting bridges in a single piece, as shown on FIG. 6D. The medical containers 100 may also include a needle 103 attached to the distal tip and a cap protecting the needle. The medical container pack may be overmolded onto the needles. Further, a plunger stopper may be arranged inside the barrel, said plunger stopper being connected to a plunger extending outside the barrel 102.

The invention also relates to a method for manufacturing a plurality of medical containers 100, this method comprising the steps of:

providing a medical container pack as above described,
breaking the connecting bridges 10 securing the flanges 50 to the supporting structure 30 so as to detach a medical containers 100 from the medical container pack.

This step preferably occurs after the barrel 102 is secured to the flange 50, and more precisely after a filling step wherein a pharmaceutical composition is poured into the barrel 102.

The step of breaking the connecting bridges 10 may be realized by exerting a distal or proximal force onto the flanges 50 or the supporting structure 30. The step of breaking the connecting bridges 10 may be realized by means of a cutting die which is applied on the breakable connecting bridges 10 or on the supporting structure 30.

The step of providing the medical container pack may comprise the step of securing the barrels 102 of the medical containers 100 onto the flanges 50 of the holding device 1.

The method may advantageously comprise the step of inserting the barrel 102 into an opening 58 of the flange 50 before securing said barrel 102 to the flange 50 by the securing means. Preferably, the barrel 102 is made of glass.

In an embodiment, the step of securing the barrel 102 to the flanges 50 comprise molding of the barrel 102 and the flanges 50 in a single piece. This step may be preceded by the positioning of needles 103 inside the mold so that the barrels 102 are overmolded onto the needles 103.

The invention claimed is:

1. A nest for supporting a plurality of medical containers, said nest comprising:
a plurality of breakable connecting bridges;
a plurality of flanges arranged in a predetermined pattern and configured to form the flanges of a plurality of medical containers, said flanges being connected to said breakable connecting bridges, the plurality of flanges having a proximal face, configured to form a push surface for applying a force on the flange in order to break the connecting bridges, and a distal face opposite said proximal face, said distal face being configured to receive a user's fingers during use of the medical containers; and
a plate-shaped supporting structure attached to said breakable connecting bridges in order to support said plurality of flanges,
wherein the flanges, the breakable connecting bridges and the supporting structure are molded in a single piece so that the flanges are integrally formed with the breakable connecting bridges and the supporting structure.

2. The nest according to claim 1, wherein each flange is surrounded by a segmented groove.

3. The nest according to claim 1, wherein each flange is connected to the supporting structure by at least two breakable connecting bridges.

4. The nest according to claim 1, wherein the supporting structure comprises a peripheral edge, said peripheral edge being connected to peripheral flanges of the plurality of flanges by breakable connecting bridges.

5. The nest according claim 1, wherein the supporting structure comprises reinforcing bars extending between adjacent rows of flanges.

6. The nest according to claim 5, wherein the reinforcing bars extend beneath said breakable connecting bridges.

7. The nest according to claim 1, wherein the nest comprises a securing means configured to secure a barrel of one of the medical containers to said flanges.

8. The nest according to claim 7, wherein the securing means comprise a guiding conduit extending from each flange, said guiding conduit being configured to receive the barrel.

9. The nest according to claim 7, wherein the securing means comprise an attachment surface configured to receive an adhesive so as to secure the barrel to the flange.

10. The nest according to claim 7, wherein the securing means comprise a friction-fit surface configured to secure the barrel to the flange.

11. The nest according to claim 7, wherein the securing means comprise a clipping element configured to fit a complementarily shaped-clipping element provided on the barrel.

12. A medical container pack comprising the nest according to claim 1 and a plurality of medical containers, wherein the plurality of medical containers have a barrel made of glass and wherein said barrel is secured to one of the flanges.

13. A method for manufacturing a medical container, comprising the steps of:
providing a medical container pack according to claim 12; and
breaking the connecting bridges securing one of the flanges to the supporting structure so as to detach the corresponding medical container from the medical container pack.

14. A medical container pack comprising the nest according to claim 1 and a plurality of medical containers, wherein the medical containers have a barrel made of a plastic material and wherein said barrels and the nest are molded in a single piece.

15. A method for manufacturing a medical container, comprising the steps of:
providing a medical container pack according to claim 14; and
securing one of the flanges to the supporting structure so as to detach the corresponding medical container from the medical container pack.

* * * * *